(12) United States Patent
Gaddi et al.

(10) Patent No.: US 9,765,161 B2
(45) Date of Patent: Sep. 19, 2017

(54) MAGNESIUM DICHLORIDE-ALCOHOL ADDUCTS AND CATALYST COMPONENTS OBTAINED THERE-FROM

(71) Applicant: Basell Poliolefine Italia S.r.l., Milan (IT)

(72) Inventors: Benedetta Gaddi, Ferrara (IT); Gianni Collina, Ferrara (IT); Daniele Evangelisti, Ferrara (IT)

(73) Assignee: Basell Poliolefine Italia S.r.l., Milan (IT)

( * ) Notice: Subject to any disclaimer, the term of this patent is extended or adjusted under 35 U.S.C. 154(b) by 208 days.

(21) Appl. No.: 14/654,201

(22) PCT Filed: Dec. 11, 2013

(86) PCT No.: PCT/EP2013/076232
§ 371 (c)(1),
(2) Date: Jun. 19, 2015

(87) PCT Pub. No.: WO2014/095523
PCT Pub. Date: Jun. 26, 2014

(65) Prior Publication Data
US 2015/0344594 A1 Dec. 3, 2015

Related U.S. Application Data

(60) Provisional application No. 61/740,317, filed on Dec. 20, 2012.

(30) Foreign Application Priority Data

Dec. 20, 2012 (EP) ..................................... 12198605

(51) Int. Cl.
C08F 110/06 (2006.01)
C07F 3/02 (2006.01)
C08F 10/06 (2006.01)

(52) U.S. Cl.
CPC .............. *C08F 110/06* (2013.01); *C07F 3/02* (2013.01); *C08F 10/06* (2013.01)

(58) Field of Classification Search
CPC ........... C08F 110/06; C08F 10/06; C07F 3/02
See application file for complete search history.

(56) References Cited

U.S. PATENT DOCUMENTS

| 4,308,170 A | 12/1981 | Mizogami et al. |
| 4,362,648 A | 12/1982 | Dietz et al. |

FOREIGN PATENT DOCUMENTS

| CN | 1143651 A | 2/1997 |
| CN | 1771266 A | 5/2006 |
| CN | 101472957 A | 7/2009 |
| EP | 0728769 A1 | 8/1996 |
| WO | WO-2007147714 A1 | 12/2007 |
| WO | WO-2009080568 A2 | 7/2009 |
| WO | WO-2012084735 A1 | 6/2012 |

*Primary Examiner* — Catherine S Branch

(57) ABSTRACT

Spherical adducts comprising a $MgCl_2$, an alcohol ROH in which R is a $C_1$-$C_{10}$ hydrocarbon group, present in a molar ratio with $MgCl_2$ ranging from 0.5 to 6 and less than 20% mol based on the mol of $MgCl_2$ of a compound of formula $Mg(OR^1)_2$ in which $R^1$ is selected from $C_1$-$C_{10}$ alkyl groups or $R^2CO$ groups in which $R^2$ is selected from C1-C6 alkyl or aryl groups.

11 Claims, No Drawings

MAGNESIUM DICHLORIDE-ALCOHOL ADDUCTS AND CATALYST COMPONENTS OBTAINED THERE-FROM

This application is the U.S. National Phase of PCT International Application PCT/EP2013/076232, filed Dec. 11, 2013, claiming benefit of priority to European Patent Application No. 12198605.3, filed Dec. 20, 2012, and benefit of priority under 35 U.S.C. §119(e) of U.S. Provisional Application No. 61/740,317 filed Dec. 20, 2012, the contents of which are incorporated herein by reference in their entirety.

FIELD OF THE INVENTION

The present invention relates to magnesium dichloride/alcohol adducts containing specific amounts of inorganic compounds having a specific particle size. The adducts of the present invention are particularly useful as precursors of catalyst components for the polymerization of olefins.

BACKGROUND OF THE INVENTION $MgCl_2$.alcohol adducts and their use in the preparation of catalyst components for the polymerization of olefins is well known in the art.

Catalyst components for the polymerization of olefins, obtained by reacting $MgCl_2$.nEtOH adducts with halogenated transition metal compounds, are described for example in U.S. Pat. No. 4,399,054. The adducts are prepared by emulsifying the molten adduct in an immiscible dispersing medium and quenching the emulsion in a cooling fluid to collect the adduct in the form of spherical particles.

In WO2009/80568 are disclosed magnesium chloride based adducts having a specific range of alcohol content and containing a specific amount of inorganic particles having a certain dimensional range are able to generate catalyst components with high polymerization activity and enhanced morphological stability. Specifically, the said document disclosed spherical adducts comprising a $MgCl_2$, an alcohol ROH in which R is a C1-C10 hydrocarbon group, present in a molar ratio with $MgCl_2$ ranging from 0.5 to 5 and less than 5% wt, based on the total weight of the adduct, of a solid inorganic compound selected from oxides or hydroxides of Si, Al, Mg, Ti and mixtures thereof. The so obtained supports led to the preparation of catalysts having improved morphological stability in terms of polymer breakages. However, by carrying out further experiment the applicant realized that the bulk density of the polymer was substantially negatively impacted.

SUMMARY OF THE INVENTION

The applicant has now found that when the same type of $MgCl_2$ alcohol adducts are added with certain types of Mg compounds generate catalyst components showing increased morphological stability (lower polymer breakages) and bulk density at a comparable level of catalyst activity.

It is therefore an object of the present invention a solid adduct comprising a $MgCl_2$, an alcohol ROH in which R is a $C_1$-$C_{10}$ hydrocarbon group, present in a molar ratio with $MgCl_2$ ranging from 0.5 to 6 and less than 20% mol based on the mol of $MgCl_2$ of a compound of formula $Mg(OR^1)_2$ in which $R^1$ is selected from $C_1$-$C_{10}$ alkyl groups or $R^2CO$ groups in which $R^2$ is selected from $C_1$-$C_6$ alkyl or aryl groups.

Preferably, the compound $Mg(OR^1)_2$ is present in an amount lower than 15%, and more preferably lower than 10% mol based on the mol of $MgCl_2$. In an especially preferred embodiment the compound $Mg(OR^1)_2$ is present in an amount lower than 8% and especially in an amount lower than 5% mol based on the mol of $MgCl_2$. The especially preferred content ranges from 1 to 4% mol based on the mol of $MgCl_2$.

Regardless of the amount, the $Mg(OR^1)_2$ compound is preferably selected from those in which $R^1$ is a $C_1$-$C_6$ linear or branched alkyl and preferably from $C_3$-$C_5$ branched alkyls. Among them t-Butyl is especially preferred. Also preferred are the compounds in which $R^1$ is $R^2CO$ with $R^2$ being a $C_1$-$C_4$ alkyl group especially ethyl.

Preferably, R is chosen among $C_1$-$C_8$ linear or branched hydrocarbon groups and more preferably among the $C_1$-$C_4$ linear hydrocarbon groups. Ethanol is especially preferred. Preferably, the number of moles of alcohol per mole of $MgCl_2$ ranges from 0.8 to 5 and more preferably from 1 to 3.5. The ethanol/Mg molar ratio from 1.5 to 3 is especially preferred.

DETAILED DESCRIPTION OF THE INVENTION

The adduct of the present invention can be prepared according to different techniques. According to a preferred method, a suitable amount of magnesium chloride, compound $Mg(OR^1)_2$ and alcohol (ROH) are contacted, then the system is heated until a molten liquid composition is formed which is then dispersed in a liquid immiscible with it so as to create an emulsion which can be then rapidly cooled in order to get solid particles of adduct preferably in spherical form. The contact between magnesium chloride, compound of formula $Mg(OR^1)_2$ and alcohol can occur in the presence or in the absence of an inert liquid immiscible with and chemically inert to the molten adduct. If the inert liquid is present it is preferred that the desired amount of alcohol is added in vapour phase. This would ensure a better homogeneity of the formed adduct. The liquid in which the adduct can be dispersed can be any liquid immiscible with and chemically inert to the molten adduct. For example, aliphatic, aromatic or cycloaliphatic hydrocarbons can be used as well as silicone oils. Aliphatic hydrocarbons such as vaseline oil are particularly preferred. After the $MgCl_2$ particles, the alcohol and the $Mg(OR^1)_2$ compound are dispersed in the liquid phase the mixture is heated at a temperature at which the adduct reaches its molten state. This temperature depends on the composition of the adduct and generally ranges from 100 to 150° C. As mentioned before the temperature is kept at values such that the adduct is completely melted. Preferably the adduct is maintained in the molten state under stirring conditions, for a time period equal to or greater than 10 hours, preferably from 10 to 150 hours, more preferably from 20 to 100 hours.

In order to obtain solid discrete particles of the adduct with suitable morphology it is possible to operate in different ways. One of the preferred possibilities is the emulsification of the adduct in a liquid medium which is immiscible with and chemically inert to it followed by the quenching carried out by contacting the emulsion with an inert cooling liquid, thereby obtaining the solidification of the particles of the adduct in spherical form.

Another preferred method for obtaining the solidification of the adduct consists in adopting the spray-cooling technique. When this option is pursued it is preferred that in the first step the magnesium chloride the $Mg(OR^1)_2$ compound and the alcohol are contacted to each other in the absence of an inert liquid dispersant. After having been melted the adduct is sprayed, through the use of the proper devices that are commercially available, in an environment having temperature so low as to cause rapid solidification of the particles. In a preferred aspect, the adduct is sprayed in a cold liquid environment and more preferably in a cold liquid hydrocarbon.

By way of these methods and in particular of the method comprising the emulsification, it is possible to obtain adduct particles in spherical or spheroidal form. Such spherical particles have a ratio between maximum and minimum diameter lower than 1.5 and preferably lower than 1.3.

The adduct of the invention can be obtained in a broad range of particle size, namely ranging from 5 to 150 microns preferably from 10 to 100 microns and more preferably from 15 to 80 microns.

Preferably, the adducts obtained according to the general method are further characterized by a DSC profile in which the highest melting Temperature (Tm) peak is higher than 90° C., preferably in the range 92-115° C.

It is also possible, but not strictly required, that also the adducts of the present invention are characterized by an X-ray diffraction spectrum in which, in the range of 2θ diffraction angles between 5° and 15°, the three main diffraction lines are present at diffraction angles 2θ of 8.8±0.2°, 9.4±0.2° and 9.8±0.2°, the most intense diffraction line being the one at 2θ=8.8±0.2°, the intensity of the other two diffraction lines being at least 0.2 times the intensity of the most intense diffraction line. Moreover, the said adduct show an X-ray diffraction spectrum in which in the range of 2θ diffraction angles between 5° and 50° the characteristic diffraction lines of the α-MgCl$_2$ are not present.

The adduct of the invention may also contain some water, preferably in an amount lower than 3% wt. The amount of water can be controlled by paying particular attention to the water content of the reactants. Both MgCl$_2$ and EtOH are in fact highly hygroscopic and tend to incorporate water in their structure. As a result, if the water content of the reactants is relatively high, the final MgCl$_2$-EtOH adducts may contain a too high water content even if water has not been added as a separate component. Means for controlling or lowering the water content in solids or fluids are well known in the art.

The adducts of the invention are converted into catalyst components for the polymerization of olefins by reacting them with a transition metal compound of one of the groups IV to VI of the Periodic Table of Elements.

Among transition metal compounds particularly preferred are titanium compounds of formula Ti(OR)$_n$X$_{y-n}$ in which n is comprised between 0 and y; y is the valence of titanium; X is halogen and R is an alkyl radical having 1-8 carbon atoms or a COR group. Among them, particularly preferred are titanium compounds having at least one Ti-halogen bond such as titanium tetrahalides or halogenalcoholates. Preferred specific titanium compounds are TiCl$_3$, TiCl$_4$, Ti(OBu)$_4$, Ti(OBu)Cl$_3$, Ti(OBu)$_2$Cl$_2$, Ti(OBu)$_3$Cl. Preferably the reaction is carried out by suspending the adduct in cold TiCl$_4$ (generally 0° C.); then the so obtained mixture is heated up to 80-130° C. and kept at this temperature for 0.5-2 hours. After that the excess of TiCl$_4$ is removed and the solid component is recovered. The treatment with TiCl$_4$ can be carried out one or more times.

The amount of the titanium compound in the final catalyst component ranges from 0.1 to 10% wt, preferably from 0.5 to 5% wt.

The reaction between transition metal compound and the adduct can also be carried out in the presence of an electron donor compound (internal donor) in particular when the preparation of a stereospecific catalyst for the polymerization of olefins is to be prepared. Said electron donor compound can be selected from esters, ethers, amines, silanes and ketones. In particular, the alkyl and aryl esters of mono or polycarboxylic acids such as for example esters of benzoic, phthalic, malonic and succinic acid are preferred. Specific examples of such esters are n-butylphthalate, di-isobutylphthalate, di-n-octylphthalate, diethyl 2,2-diisopropylsuccinate, diethyl 2,2-dicyclohexyl-succinate, ethyl-benzoate and p-ethoxy ethyl-benzoate. Moreover, can be advantageously used also the 1,3 diethers of the formula:

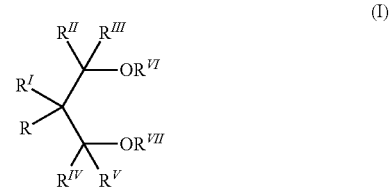

(I)

wherein R, $R^I$, $R^{II}$, $R^{III}$, $R^{IV}$ and $R^V$ equal or different to each other, are hydrogen or hydrocarbon radicals having from 1 to 18 carbon atoms, and $R^{VI}$ and $R^{VII}$, equal or different from each other, have the same meaning of R—$R^V$ except that they cannot be hydrogen; one or more of the R—$R^{VII}$ groups can be linked to form a cycle. The 1,3-diethers in which $R^{VI}$ and $R^{VII}$ are selected from C$_1$-C$_4$ alkyl radicals are particularly preferred.

The electron donor compound is generally present in molar ratio with respect to the magnesium comprised between 1:4 and 1:60.

Preferably, the particles of the solid catalyst components have substantially the same size and morphology as the adducts of the invention generally comprised between 5 and 150 μm.

Before the reaction with the transition metal compound, the adducts of the present invention can also be subjected to a dealcoholation treatment aimed at lowering the alcohol content and increasing the porosity of the adduct itself. The dealcoholation can be carried out according to known methodologies such as those described in EP-A-395083. Depending on the extent of the dealcoholation treatment, partially dealcoholated adducts can be obtained having an alcohol content generally ranging from 0.1 to 2.6 moles of alcohol per mole of MgCl$_2$. After the dealcoholation treatment the adducts are reacted with the transition metal compound, according to the techniques described above, in order to obtain the solid catalyst components.

The solid catalyst components according to the present invention show a surface area (by B.E.T. method) generally between 10 and 500 m$^2$/g and preferably between 20 and 350 m$^2$/g, and a total porosity (by B.E.T. method) higher than 0.15 cm$^3$/g preferably between 0.2 and 0.6 cm$^3$/g.

The catalyst components of the invention form catalysts for the polymerization of alpha-olefins CH$_2$=CHR, wherein R is hydrogen or a hydrocarbon radical having 1-12 carbon atoms, by reaction with Al-alkyl compounds. The alkyl-Al compound can be of the formula AlR$_{3-z}$X$_z$ above, in which R is a C1-C15 hydrocarbon alkyl radical, X is halogen preferably chlorine and z is a number 0≤z<3. The Al-alkyl compound is preferably chosen among the trialkyl aluminum compounds such as for example trimethylaluminum triethylaluminum, triisobutylaluminum, tri-n-butylaluminum, tri-n-hexylaluminum, tri-n-octylaluminum. It is also possible to use alkylaluminum halides, alkylaluminum hydrides or alkylaluminum sesquichlorides such as $AlEt_2Cl$ and $Al_2Et_3Cl_3$ optionally in mixture with said trialkyl aluminum compounds.

The Al/Ti ratio is higher than 1 and is generally comprised between 50 and 2000.

It is possible to use in the polymerization system an electron donor compound (external donor) which can be the same or different from the compound that can be used as internal donor disclosed above. In case the internal donor is an ester of a polycarboxylic acid, in particular a phthalate, the external donor is preferably selected from the silane compounds containing at least a Si—OR link, having the formula $R_a^1R_b^2Si(OR^3)_c$, where a and b are integer from 0 to 2, c is an integer from 1 to 3 and the sum (a+b+c) is 4; $R^1$, $R^2$, and $R^3$, are alkyl, cycloalkyl or aryl radicals with 1-18 carbon atoms. Particularly preferred are the silicon compounds in which a is 1, b is 1, c is 2, at least one of $R^1$ and $R^2$ is selected from branched alkyl, cycloalkyl or aryl groups with 3-10 carbon atoms and $R^3$ is a $C_1$-$C_{10}$ alkyl group, in particular methyl. Examples of such preferred silicon compounds are methylcyclohexyldimethoxysilane, diphenyldimethoxysilane, methyl-t-butyldimethoxysilane, dicyclopentyldimethoxysilane. Moreover, are also preferred the silicon compounds in which a is 0, c is 3, $R^2$ is a branched alkyl or cycloalkyl group and $R^3$ is methyl. Examples of such preferred silicon compounds are cyclohexyltrimethoxysilane, t-butyltrimethoxysilane and thexyltrimethoxysilane.

Also the cyclic ethers such as tetrahydrofurane, and the 1,3 diethers having the previously described formula can be used as external donor.

As previously indicated the components of the invention and catalysts obtained therefrom find applications in the processes for the (co)polymerization of olefins of formula $CH_2=CHR$ in which R is hydrogen or a hydrocarbon radical having 1-12 carbon atoms.

The catalysts of the invention can be used in any of the olefin polymerization processes known in the art. They can be used for example in slurry polymerization using as diluent an inert hydrocarbon solvent or bulk polymerization using the liquid monomer (for example propylene) as a reaction medium. Moreover, they can also be used in the polymerization process carried out in gas-phase operating in one or more fluidized or mechanically agitated bed reactors.

The polymerization is generally carried out at temperature of from 20 to 120° C., preferably of from 40 to 80° C. When the polymerization is carried out in gas-phase the operating pressure is generally between 0.1 and 10 MPa, preferably between 1 and 5 MPa. In the bulk polymerization the operating pressure is generally between 1 and 6 MPa preferably between 1.5 and 4 MPa.

The catalysts of the invention are very useful for preparing a broad range of polyolefin products. Specific examples of the olefinic polymers which can be prepared are: high density ethylene polymers (HDPE, having a density higher than 0.940 g/cc), comprising ethylene homopolymers and copolymers of ethylene with alpha-olefins having 3-12 carbon atoms; linear low density polyethylenes (LLDPE, having a density lower than 0.940 g/cc) and very low density and ultra low density (VLDPE and ULDPE, having a density lower than 0.920 g/cc, to 0.880 g/cc) consisting of copolymers of ethylene with one or more alpha-olefins having from 3 to 12 carbon atoms, having a mole content of units derived from the ethylene higher than 80%; isotactic polypropylenes and crystalline copolymers of propylene and ethylene and/or other alpha-olefins having a content of units derived from propylene higher than 85% by weight; copolymers of propylene and 1-butene having a content of units derived from 1-butene comprised between 1 and 40% by weight; heterophasic copolymers comprising a crystalline polypropylene matrix and an amorphous phase comprising copolymers of propylene with ethylene and or other alpha-olefins.

In particular, it has been noticed that the catalyst components obtained from the said adducts generate during polymerization a very reduced content of broken polymer particles in comparison with the catalyst obtained from adducts not containing the inorganic solid compound. This reduced content of broken polymer particles greatly facilitates the run of the polymerization plants avoiding the formation of fines.

The following examples are given to further illustrate without limiting in any way the invention itself.

EXAMPLES

Characterization

The properties reported below have been determined according to the following methods:

Fraction Soluble in Xylene.

(XS) The solubility in xylene at 25° C. was determined according to the following method: About 2.5 g of polymer and 250 ml of o-xylene were placed in a round-bottomed flask provided with cooler and a reflux condenser and kept under nitrogen. The mixture obtained was heated to 135° C. and was kept under stirring for about 60 minutes. The final solution was allowed to cool to 25° C. under continuous stirring, and was then filtered. The filtrate was then evaporated in a nitrogen flow at 140° C. to reach a constant weight. The content of said xylene-soluble fraction is expressed as a percentage of the original 2.5 grams.

Average Particle Size of the Polymers

Determined through the use Tyler Testing Sieve Shaker RX-29 Model B available from Combustion Engineering Endecott provided with a set of six sieves, according to ASTM E-11-87, of number 5, 7, 10, 18, 35, and 200 respectively.

Example 1

A 1 liter reactor was loaded with 100 g of anhydrous MgCl2, 144 g of EtOH, and 5 g of $Mg(CH_3COO)_2*4H_2O$ The temperature was raised up to 125° C. and kept at this value for 5 hours. After that, the resulting melt was emulsified with ROL OB55 AT vaseline oil continuously introduced at 125° C. in an emulsifier, the stirring was brought to 1500 rpm and kept at that value for five minutes while continuously feeding the obtained emulsion into a stirred reactor containing cold hexane under stirring at 1000 rpm. The solid spherical catalyst support is then crystallized washed and dried, collecting a material having a composition of 54.6% EtOH, 11.1% Mg, 32.4% Cl by weight and a P50 of 55 micron.

The solid catalyst component was prepared by following the procedure below.

Preparation of the Solid Catalyst Component

Into a 2 liter steel reactor provided with stirrer, 1500 cm$^3$ of $TiCl_4$ at 0° C. were introduced; at room temperature and whilst stirring 45 g of the above adduct were introduced together with an amount of diisobutylphthalate (DIBP) as internal donor so as to give a Mg/donor molar ratio of 8. The whole was heated to 100° C. over 90 minutes and these conditions were maintained over 60 minutes. The stirring was stopped and after 15 minutes the liquid phase was separated from the settled solid maintaining the temperature at 100° C. A further treatment of the solid were carried out adding 1500 cm$^3$ of TiCl$_4$ and heating the mixture at 110° C. over 10 min. and maintaining said conditions for 30 min under stirring conditions (500 rpm). The stirring was then discontinued and after 15 minutes the liquid phase was separated from the settled solid maintaining the temperature at 110° C. Two further treatments of the solid were carried out adding 1500 cm$^3$ of TiCl$_4$ and heating the mixture at 120° C. over 10 min. and maintaining said conditions for 60 min under stirring conditions (500 rpm). The stirring was then discontinued and after 15 minutes the liquid phase was separated from the settled solid maintaining the temperature at 120° C. Thereafter, 3 washings with 1500 cm$^3$ of anhydrous hexane at 60° C. and 3 washings with 1500 cm$^3$ of anhydrous hexane at room temperature were carried out. The solid catalyst component obtained was then dried under vacuum in nitrogen environment at a temperature ranging from 40-45° C. The analysis showed a titanium content of 2.6%, a Mg content of 16.6%, and a DIBP content of 8.8%, and a P50 of 52.7 microns.

Propylene Polymerization Test

A 4 liter steel autoclave equipped with a stirrer, pressure gauge, thermometer, catalyst feeding system, monomer feeding lines and thermostatting jacket, was used. The reactor was charged with 0.01 gr. of solid catalyst component 0.76 g of TEAL, 0.063 grams of cycloexylmethyldimetoxy silane, 3.2 l of propylene, and 2.0 l of hydrogen. The system was heated to 70° C. over 10 min. under stirring, and maintained under these conditions for 120 min. At the end of the polymerization, the polymer was recovered by removing any unreacted monomers and was dried under vacuum. The results are reported in table 1.

Comparative 1

The same procedure described for the preparation of the support of example 1 was repeated with the difference that Mg(CH$_3$COO)$_2$ was not used. The final adduct had P50 particle size of 68.0 µm. The catalyst was prepared and the polymerization test was carried out as described in Example 1. The polymerization results are reported in table 1.

Example 2

The same procedure described fore the preparation of the support of example 1 was repeated with the difference that 4 grams of Mg(t-BuO)$_2$ was used instead of Mg(CH$_3$COO)$_2$. The final adduct had P50 particle size of 61.4 µm. The catalyst was prepared and the polymerization test was carried out as described in Example 1. The polymerization results are reported in table 1.

Example 3

The same procedure described for the preparation of the support of example 2 was repeated with the difference that 8 grams of Mg(t-BuO)$_2$ was used instead of Mg(CH$_3$COO)$_2$. The final adduct had P50 particle size of 78.7 µm. The catalyst was prepared and the polymerization test was carried out as described in Example 1. The polymerization results are reported in table 1.

Comparative 2

The same procedure described for the preparation of the support of example 2 was repeated with the difference that Mg(t-BuO)$_2$ was not used. The final adduct had P50 particle size of 74.1 µm. The catalyst was prepared and the polymerization test was carried out as described in Example 1. The polymerization results are reported in table 1.

TABLE 1

| Example | Activity Kg/g | Xylene Insol. % | Bulk Density g/cm$^3$ | Breakages % |
|---|---|---|---|---|
| 1 | 66.0 | 97.6 | 0.447 | 3.3 |
| Comp. 1 | 70.0 | 97.7 | 0.428 | 5.5 |
| 2 | 71.5 | 97.9 | 0.451 | 4.1 |
| 3 | 63.2 | 97.8 | 0.434 | 4.5 |
| Comp. 2 | 77.3 | 98.2 | 0.417 | 6.5 |

What is claimed is:

1. A solid adduct comprising MgCl$_2$, an alcohol ROH in which R is a C$_1$-C$_{10}$ hydrocarbon group present in a molar ratio with MgCl$_2$ of 0.5 to 6, and greater than 1% mol of a compound of formula Mg(OR$^1$)$_2$, in which R$^1$ is selected from C$_1$-C$_{10}$ alkyl groups or R$^2$CO groups in which R$^2$ is selected from C$_1$-C$_6$ alkyl or aryl groups.

2. The solid adduct of claim 1, in which the compound Mg(OR$^1$)$_2$ is present in an amount lower than 15% based on the mol of MgCl$_2$.

3. The solid adduct of claim 1, in which the Mg(OR$^1$)$_2$ compound is selected from those in which R$^1$ is a C$_1$-C$_6$ linear or branched alkyl.

4. The solid adduct of claim 1, in which the Mg(OR$^1$)$_2$ compound is selected from those in which R$^1$ is a C$_3$-C$_5$ branched alkyl.

5. The solid adduct of claim 1, in which the Mg(OR$^1$)$_2$ compound is selected from compounds in which R$^1$ is R$^2$CO with R$^2$ being a C$_1$-C$_4$ alkyl group.

6. The solid adduct of claim 5, in which R$^2$ is methyl.

7. The solid adduct of claim 1, in which R is chosen among C$_1$-C$_8$ linear or branched hydrocarbon groups.

8. The solid adduct of claim 1, in which the number of moles of alcohol per mole of MgCl$_2$ ranges from 0.8 to 4.

9. A method for forming a catalyst component comprising reacting the solid adduct of claim 1 with a transition metal compound of Groups IV-VI of the Periodic Table of Elements.

10. The method of claim 9, wherein the catalyst component is reacted with an Al-alkyl compound optionally in the presence of an external electron donor compound for the polymerization of alpha-olefins CH$_2$=CHR, wherein R is hydrogen or a hydrocarbon radical having 1-12 carbon atoms.

11. The solid adduct of claim 1, comprising 1-4% mol of a compound of formula Mg(OR$^1$)$_2$.

* * * * *

UNITED STATES PATENT AND TRADEMARK OFFICE
CERTIFICATE OF CORRECTION

PATENT NO. : 9,765,161 B2  
APPLICATION NO. : 14/654201  
DATED : September 19, 2017  
INVENTOR(S) : Benedetta Gaddi et al.

Page 1 of 1

It is certified that error appears in the above-identified patent and that said Letters Patent is hereby corrected as shown below:

On the Title Page

(57)      Line 6      In the Abstract, delete "C1-C6" and insert --$C_1$-$C_6$--

In the Specification

| | | |
|---|---|---|
| Column 1 | Line 41 | Delete "C1-C10" and insert --$C_1$-$C_{10}$-- |
| Column 3 | Line 21 | Delete "(Tm)" and insert --($T_m$)-- |
| Column 3 | Line 25 | Delete "20" and insert --2θ-- |
| Column 4 | Line 64 | Delete "C1-C15" and insert --$C_1$-$C_{15}$-- |
| Column 6 | Line 46 | Delete "MgCl2," and insert --$MgCl_2$,-- |
| Column 6 | Line 46 | After "Mg(CH$_3$COO)$_2$*4H$_2$O", insert --.-- |
| Column 7 | Line 47 | Delete "fore" and insert --for-- |

Signed and Sealed this  
Fourteenth Day of January, 2020

Andrei Iancu  
*Director of the United States Patent and Trademark Office*